(12) United States Patent
Singh B et al.

(10) Patent No.: US 7,184,519 B2
(45) Date of Patent: Feb. 27, 2007

(54) COMPACT BUMPER SYSTEM FOR IMAGING DEVICE

(75) Inventors: Ram Kishan Singh B, Karnataka (IN); Bindu Santha Philip, Karnataka (IN); Vipin J. Pillai, Karnataka (IN); David Ellis Barker, Salt Lake City, UT (US); Lonnie Weston, Salt Lake City, UT (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 652 days.

(21) Appl. No.: 10/675,127

(22) Filed: Sep. 30, 2003

(65) Prior Publication Data

US 2005/0070779 A1    Mar. 31, 2005

(51) Int. Cl.
*H05G 1/02*    (2006.01)

(52) U.S. Cl. .................. 378/117; 378/95; 378/177; 378/189; 378/197

(58) Field of Classification Search ................ 378/95, 378/117, 177, 189, 197
See application file for complete search history.

(56) References Cited

U.S. PATENT DOCUMENTS

| | | | | |
|---|---|---|---|---|
| 4,811,725 A | * | 3/1989 | Grasser | 601/4 |
| 4,969,170 A | * | 11/1990 | Kikuchi et al. | 378/91 |
| 4,987,583 A | * | 1/1991 | Travanty et al. | 378/91 |
| 5,056,365 A | * | 10/1991 | Gray et al. | 73/432.1 |
| 5,097,495 A | * | 3/1992 | Gray et al. | 378/117 |
| 5,105,455 A | * | 4/1992 | Kato et al. | 378/117 |
| 5,651,044 A | * | 7/1997 | Klotz et al. | 378/117 |
| 6,561,301 B1 | * | 5/2003 | Hayashi et al. | 180/274 |

* cited by examiner

*Primary Examiner*—Edward J. Glick
*Assistant Examiner*—Thomas R. Artman
(74) *Attorney, Agent, or Firm*—McAndrews, Held & Malloy, Ltd.; Peter J. Vogel; Michael A. Dellapenna

(57) ABSTRACT

A medical imaging system including an imaging device and a patient positioning area in close proximity to the imaging device. A protective bumper is attached to, and conforms to a shape of the imaging device. The system may also include a detection system that has a pressure sensing device.

13 Claims, 6 Drawing Sheets

COMPACT BUMPER SYSTEM FOR IMAGING DEVICE

BACKGROUND OF THE INVENTION

Embodiments of the present invention generally relate to improvements in a medical imaging system, and more particularly relate to a compact bumper system used with a medical imaging system.

Various imaging modalities, such as MR, CT, ultrasound, x-ray, and PET, are used in diagnostic and/or surgical procedures. Typically, imaging systems include an imaging device proximate a patient positioning area, and a control and display unit, which is used to operate and control the imaging device. The imaging device may be a camera, x-ray detector/emitter, gamma camera, ultrasound transducer, or various other systems used to image a patient.

A patient to be imaged is positioned within the patient positioning area. For example, as shown in FIG. 5, the patient positioning area may include a support table 98 or chair to support and stabilize the patient. The imaging device, which may include a detector 110 and/or an emitter 114, may be configured to translate toward and away from the patient in an axial X direction and/or a radial R direction.

Many x-ray imaging systems include an x-ray source, a detector, and a positioning arm, such as a C-arm, supporting the x-ray source and the detector. In operation, an imaging table, on which a patient is positioned, is located between the x-ray source and the detector. The x-ray source typically emits a conical beam of radiation, such as x-rays, toward the patient. The conical beam has a theoretical central beam. The radiation typically passes through the patient positioned on the imaging table and impinges on the detector. As the radiation passes through the patient, anatomical structures of different densities inside the patient cause intensity variances in the radiation received at the detector. The detector then translates the radiation variances into an image that may be employed for clinical evaluations. Typically, the x-ray source is directly mounted to a distal end of the C-arm while the x-ray detector is mounted to another distal end of the C-arm. The x-ray source is positioned such that emitted x-rays are received by the x-ray detector.

The C-arm is mounted to the support structure, which may be mobile or fixed, through a bearing assembly. The bearing assembly allows the C-arm to rotate relative to the support structure. Therefore, anatomical structures of a patient positioned between the x-ray source and the x-ray detector may be imaged from different angles and perspectives. That is, the x-ray source and the x-ray detector rotate around the patient thereby imaging anatomical structures of the patient from various angles and perspectives.

During operation of an imaging system, it is often desirable to have the imaging device, such as an x-ray detector, as close as possible to the patient to improve the resolution and quality of the resulting images. With respect to x-ray imaging systems, placing the detector in close proximity to the patient helps to eliminate air gaps between the patient and the detector that may cause scattering of the x-rays. Further, as mentioned above, an imaging device may be moved relative to a patient thereby increasing the possibility of the imaging device colliding with the patient. For example, a C-arm of an imaging system is often rotated or maneuvered around a patient to obtain various imaging angles and perspectives. Therefore, with motorized mobile C-arms, there is a danger that the detector may contact or collide with the patient.

FIG. 3 illustrates a side view of a general imaging device 96. The imaging device 96 may be an x-ray detector, gamma camera, ultrasound transducer, or various other types of imaging devices that may be used with various imaging modalities. As shown in FIG. 3, collisions against the imaging device 96 may occur in the axial X, radial R, and diagonal D directions. In addition, collisions may occur when the detector rubs against the patient, thereby potentially causing harm to the patient.

In order to protect the patient from such collisions, some imaging systems include pads or protective bumpers. One such system uses a circular profile air (or fluid) bumper that is mounted around the outer wall of the detector. For example, FIG. 6 illustrates a cross sectional view of a center portion of a general imaging device 96 having a main body 92. The imaging device 96 includes a circular profile bumper 94 adjacent to, and encircling the main body 92. A circular profile, however, has some inherent disadvantages due to its geometry.

As the surface area of a bumper increases, the bumper's ability to distribute and absorb an impact force increases. A bumper having a circular profile has a low surface area to volume ratio. In order to provide an adequate level of load distribution, a circular bumper typically needs a relatively large diameter, which is a disadvantage because space is limited in various medical procedures.

Additionally, a circular or oblong profile constrains the size and use of the bumper. When a fluid filled bumper experiences an impact, the force of the impact causes a change in the internal pressure of the bumper. Typically, the size of the pressure fluctuation caused by an impact will increase as the volume of the bumper decreases. A smaller bumper, therefore, is more pressure sensitive to an impact force. Because an imaging device may be controlled in response to bumper pressure fluctuation measurements, a more pressure sensitive bumper may be preferred. Also, a circular (or oblong) profile limits protection along any one axis, either axially or radially, depending on the mounting position of the bumper.

Therefore a need exists for a minimally intrusive contact detection and impact load absorption system. A need also exists for a system that detects and absorbs contact/collisions in multiple directions, and that provides better load distribution and better pressure sensitivity.

BRIEF SUMMARY OF THE INVENTION

In accordance with an embodiment of the present invention, a medical imaging system is provided that includes an imaging device and a patient positioning area in close proximity to the imaging device. The imaging device is configured to move within the patient positioning area. A protective bumper that conforms to a shape of the imaging device is attached to the imaging device.

Another embodiment of the present invention includes a medical imaging device having a main body extending from a support structure. The main body has a distal end with a lower surface and a lateral surface. An L-shaped cushioned bumper is attached to a portion of the distal end of the main body. The L-shaped cushioned bumper, which conforms to a shape of the distal end of the main body, has a lower member integrally formed with an upper member. The lower member extends over the lower surface of the distal end, and said upper member extends over the lateral surface of the imaging end.

Another embodiment of the present invention includes a medical imaging device having a main body extending from a support structure. The main body has a distal end with a lower surface and a lateral surface. A fluid filled L-shaped cushioned bumper is attached to a portion of the distal end of the main body. A detection system that includes a pressure sensing device is in contact with the fluid contained in the L-shaped cushioned bumper Another embodiment of the present invention includes a medical imaging device having a main body extending from a support structure. The main body has a distal end with a lower surface and a lateral surface. A first cushioned bumper is positioned around at least a portion of the lateral surface and a second cushioned bumper is positioned over at least a portion of the lower surface.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

DETAILED DESCRIPTION OF THE INVENTION

Figure 1:
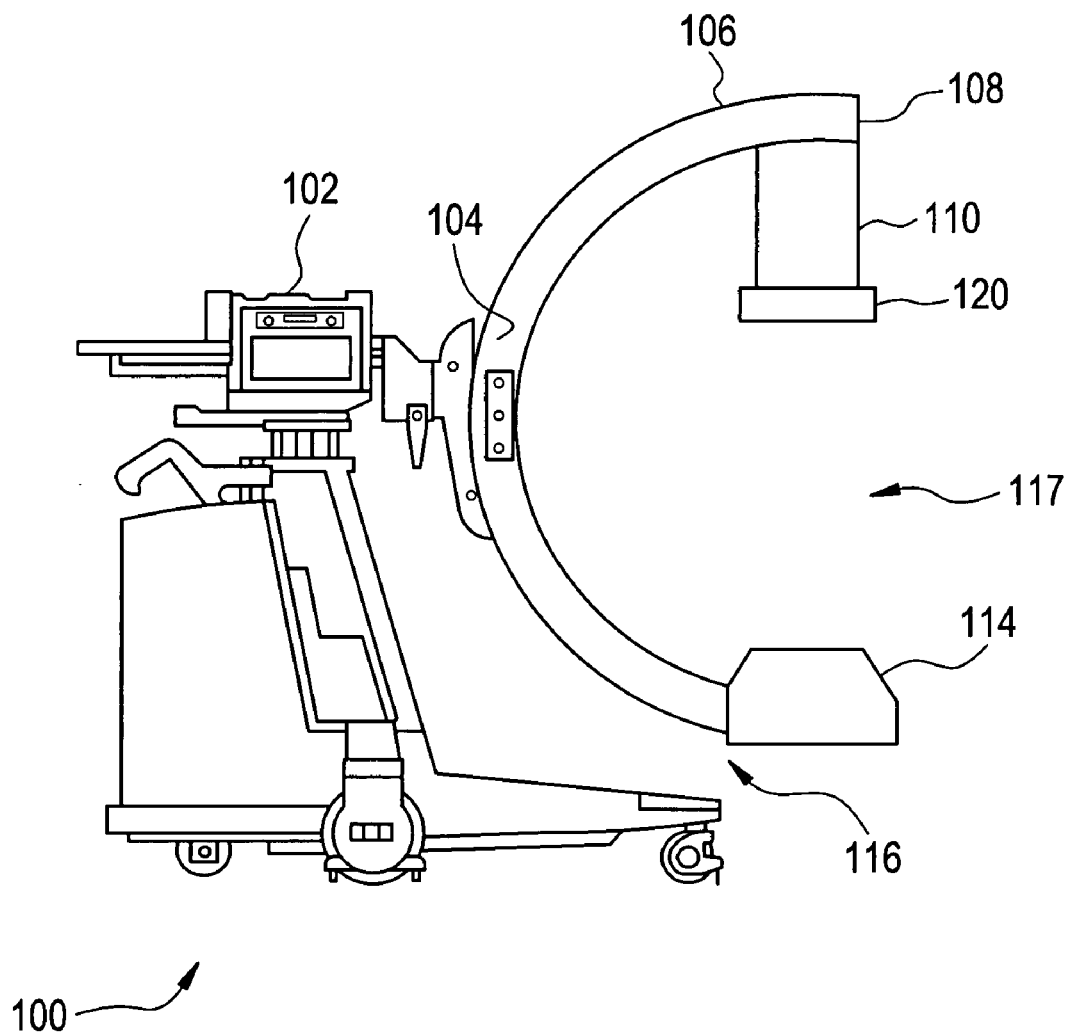
FIG. 1 illustrates an x-ray system according to an embodiment of the present invention.
Figure 5:
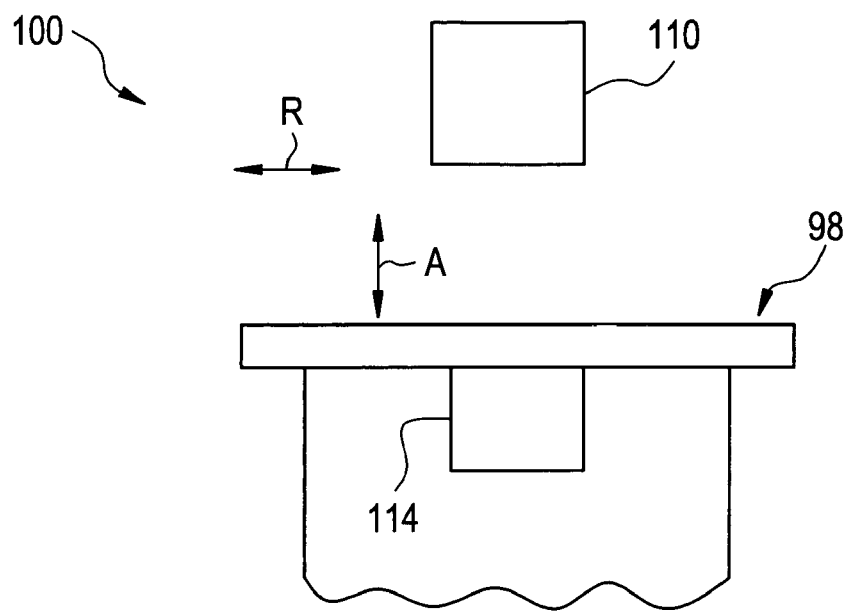
FIG. 5 illustrates a side view of a general imaging system.
Figure 6:
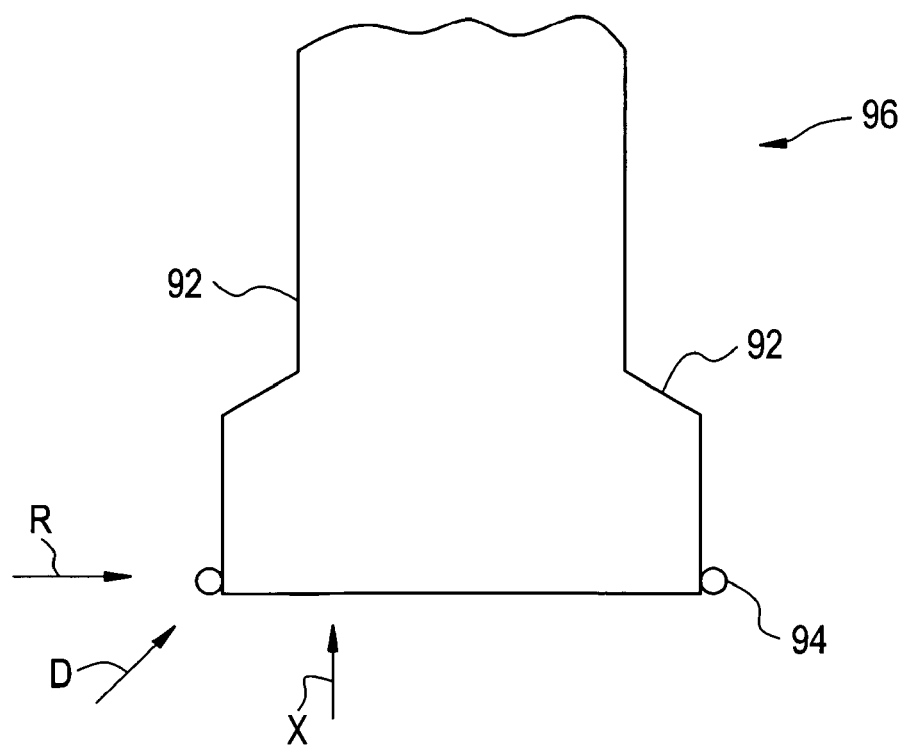
FIG. 6 illustrates a cross-sectional view of a center portion of a prior imaging device.

FIG. 1 illustrates an imaging system 100 according to embodiment of the present invention. In FIG. 1, the imaging system 100 is an x-ray imaging system including a mobile support structure 102, a bearing assembly 104 a positioning arm, or C-arm 106. An x-ray detector 110 is connected to one distal end 108 of the C-arm 106, and an x-ray source 114 is connected to another distal end 116 of the C-arm 106. A patient positioning area 117 is located between the x-ray detector 110 and the x-ray source 114. (As shown in FIG. 5, the patient positioning area may include a support table 98 or chair to support and stabilize the patient.) The mobile support structure 102 supports the bearing assembly 104. Optionally, the support structure may be fixed and the x-ray emitter and detector may be replaced with various other imaging devices. That is, the C-arm may be used with various other modalities, and is not limited to x-ray fluoroscopy. Also, instead of the C-arm, the x-ray detector 110 and source 114 may be configured to be linearly actuated to and from a patient supported on a support table. For example, an imaging device may be oriented above and/or below a patient lying on a support table (See FIG. 5). Alternatively, the imaging device may be oriented to the side(s) of a patient sitting in a chair or standing up.

Figure 2:
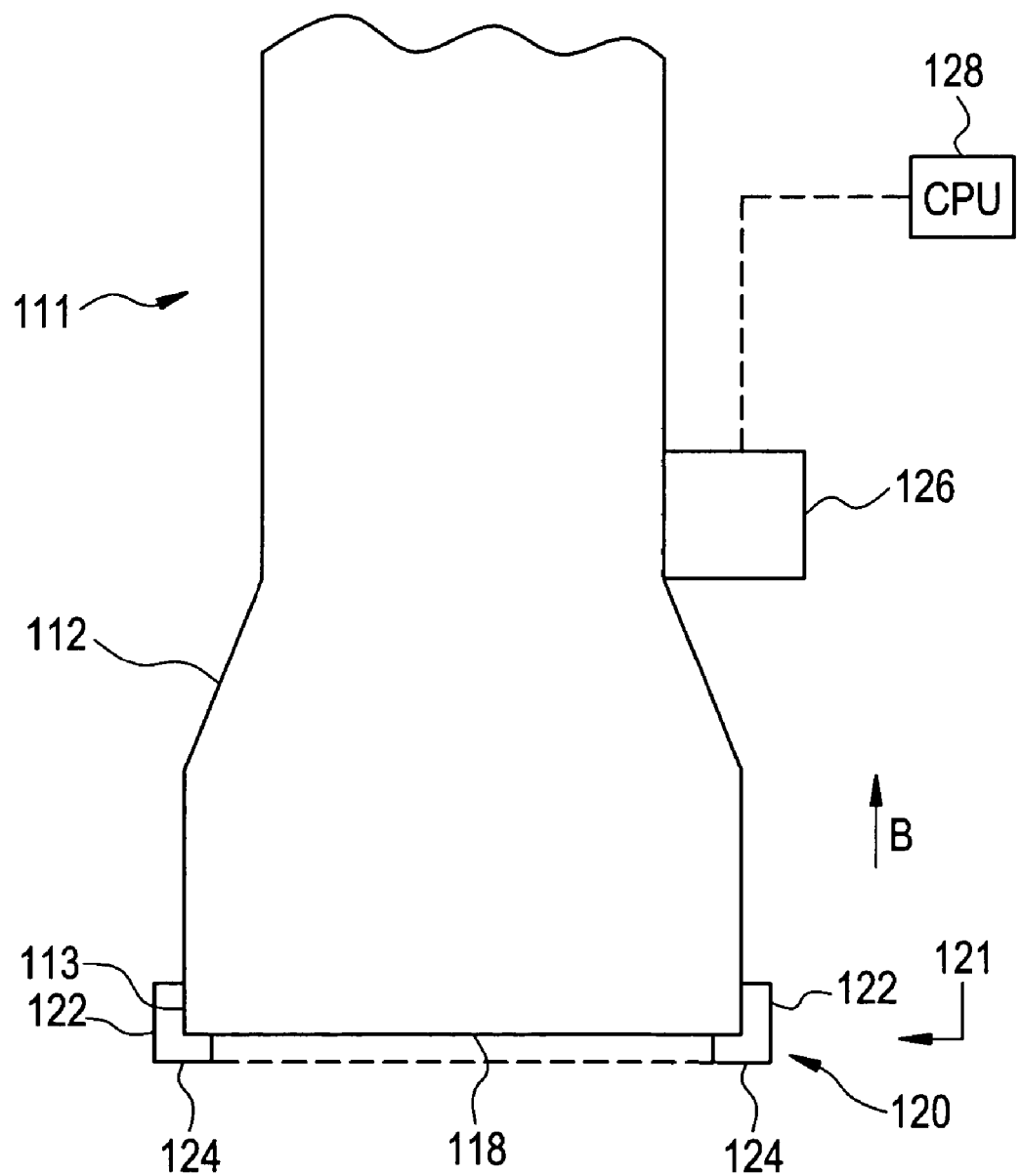
FIG. 2 illustrates a cross-sectional view of a center portion of an imaging device according to an embodiment of the present invention.

FIG. 2 illustrates a cross-sectional view of a center portion of an imaging device according to an embodiment of the present invention. As illustrated in FIG. 2, the imaging device 111, which may be, but is not limited to an x-ray detector (such as detector 110), emitter (such as emitter 114), ultrasound transducer, gamma camera, optical camera, electromagnetic field generator or sensor, or the like, has a main body 112 extending from a support structure, such as the distal end 108 of the C-arm 106, as shown in FIG. 1. The main body 112 has a distal end 121 defining a circular edge 118. The area of the circle defined by the edge 118 defines a lower surface of the distal end 121 of the main body 112. The outer surface of the distal end 121 of the main body 112 may be called the lateral surface 113 of the main body. An L-shaped cushioned bumper 120 is attached to the imaging device 111, and is located at the edge 118. The bumper 120 has an upper lip, or member, 122 integrally formed with a lower lip, or member, 124. The first lip 122 is vertically oriented in the direction of line B and adjacent to the lateral surface 113 of the main body 112 while the second lip 124 extends laterally across the detector edge 118 (or a portion of the lower surface of the distal end 121 of the main body 112). The L-shaped cushioned bumper 120 may be integrally formed with the imaging device 111 and/or permanently or removably fastened to the imaging device 111. For example, the L-shaped cushioned bumper 120 may be glued, bonded, or otherwise attached to the imaging device 111. Optionally, the imaging device 111 may include latches, clamps, or other such features that engage corresponding structures on the interior of the L-shaped cushioned bumper 120.

Figure 8:
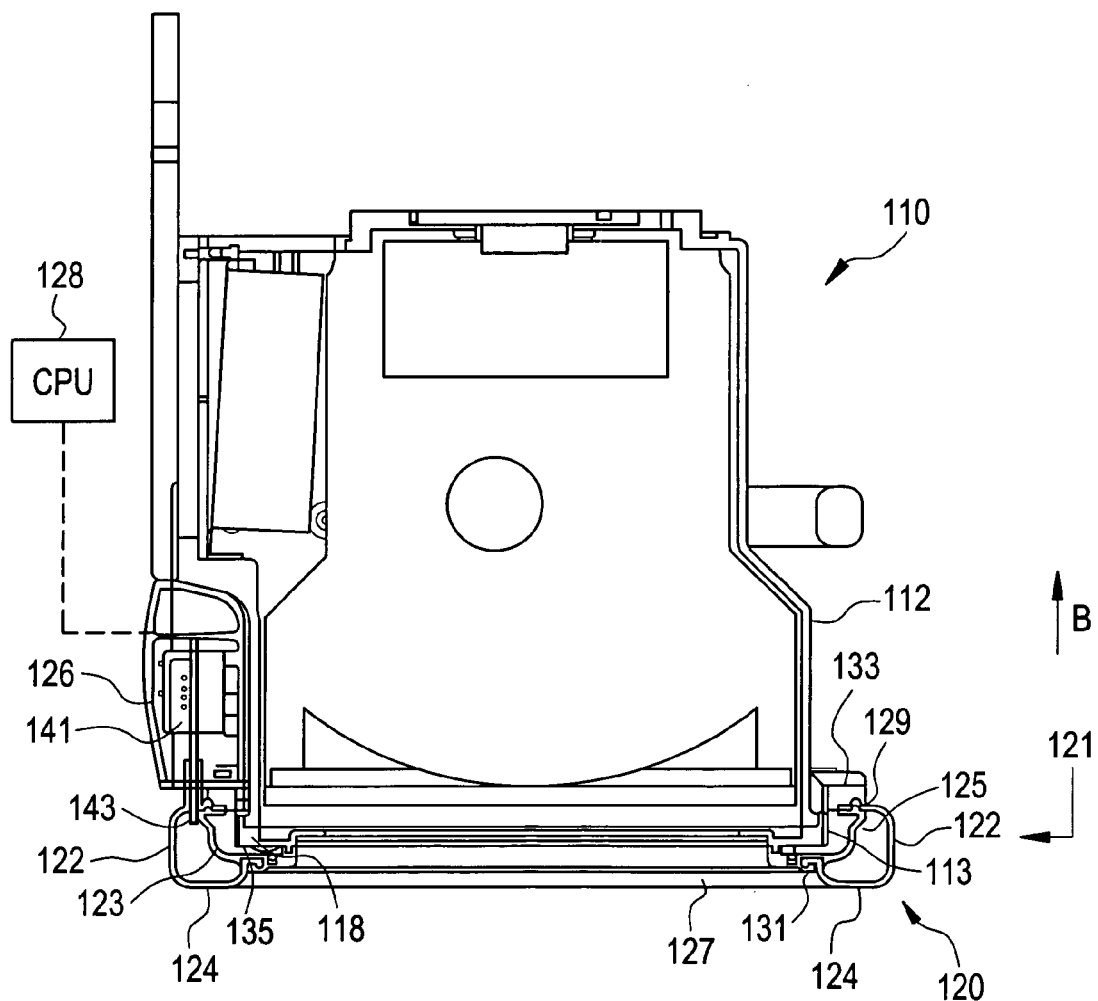
FIG. 8 illustrates an x-ray detector according to an embodiment of the invention.

FIG. 8 illustrates an x-ray detector 110 according to an embodiment of the invention. The detector 110 has a main body 112 with a distal end 121 defining a circular edge 118. The area of the circle defined by the edge 118 defines a lower surface of the distal end 121 of the main body 112. The outer surface of the distal end 121 of the main body 112 may be called the lateral surface 113 of the main body. An L-shaped cushioned bumper 120 is attached to the detector 110, and is located at the edge 118. The bumper 120 has an upper lip, or member, 122 integrally formed with a lower lip, or member, 124. The first lip 122 is vertically oriented in the direction of line B and adjacent to the lateral surface 113 of the main body 112 while the second lip 124 extends laterally across the detector edge 118 (or a portion of the lower surface of the distal end 121 of the main body 112). A mounting frame 123 having an upper base 125 and lower base 127 is located at the distal end 121 of the main body 112. The upper base 125 extends above the detector edge 118 in the direction of line B. The lower base 127 extends below the detector edge 118 in the opposite direction of line B. The upper base 125 includes an upper flange 129 extending laterally towards the main body 112 and parallel to the plane including the circle defined by the detector edge 118. The lower base 127 includes a lower flange 131, extending in the opposite direction of the upper flange 129, and parallel to the plane including the circle defined by the detector edge 118. A portion of the upper lip 122 of the bumper 120 is clamped to the upper flange 129 by an upper clamp ring 133 mounted around the main body 112. A portion of the lower lip 124 is clamped to the lower flange by a lower clamp ring 135 mounted to the detector edge 118.

Figure 7:
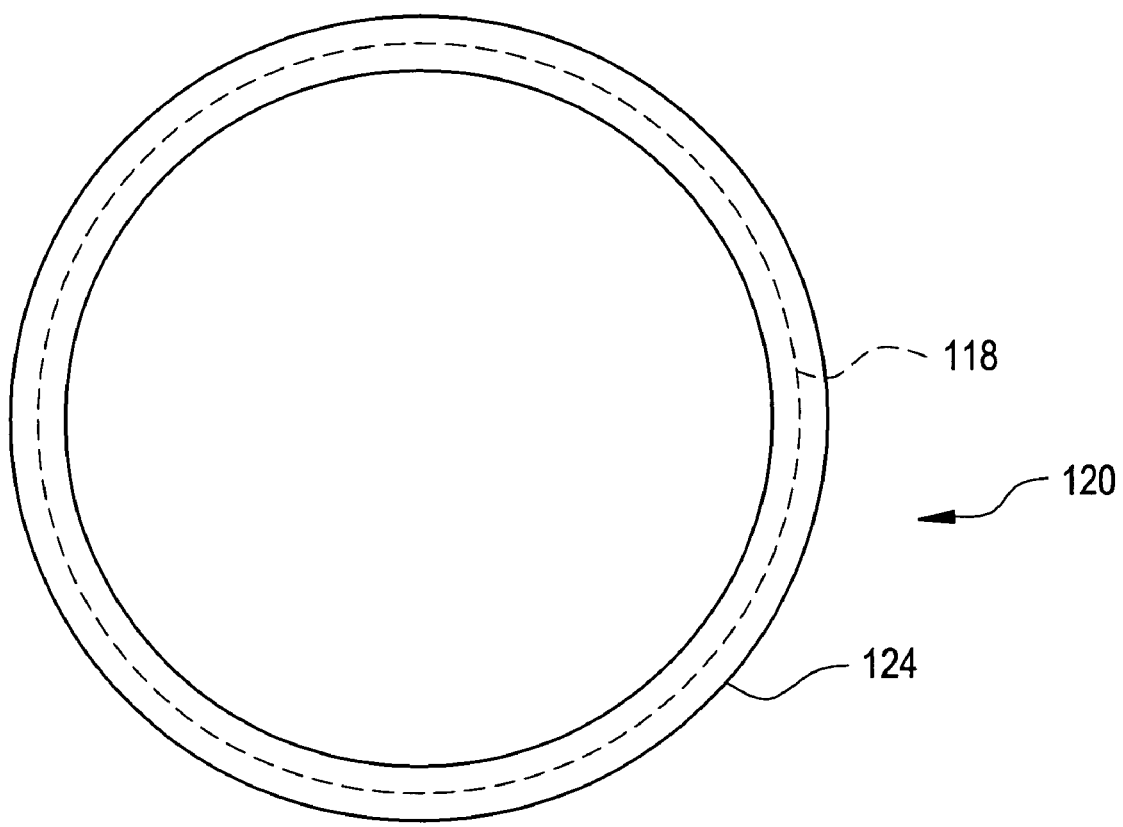
FIG. 7 illustrates an axial view of the distal end of an imaging device, having a circular axial cross-section, according to an embodiment of the invention.

The axial cross section of the imaging device of the current invention may be circular, rectangular, or various other shapes and sizes exhibited by various other imaging devices. FIG. 7 illustrates an axial view of the distal end 121 of an imaging device, having a circular axial cross-section, according to an embodiment of the invention. As illustrated in FIG. 7, the lower lip 124 of an L-shaped cushioned bumper 120 extends laterally across the detector edge 118 (perforated line).

The L-shaped cushioned bumper 120 may be a fluid filled bladder made of silicone rubber. Optionally, the L-shaped cushioned bumper 120 may be formed of various viscoelastic materials, foam, and the like. Preferably, the L-shaped cushioned bumper 120 is formed of a material that meets FDA requirements for [ ], may be cleaned with chemicals typically used in the medical industry, and is soft enough to absorb an impact of the imaging device with a patient or structure. The L-shaped cushioned bumper 120, which may surround a fluid such as air, water, and the like, may also include an outer membrane, such as a fluid tight plastic. As shown in FIG. 1, the L-shaped cushioned bumper 120 conforms to the contours of the distal end 121 of the imaging device 111.

Figure 4:
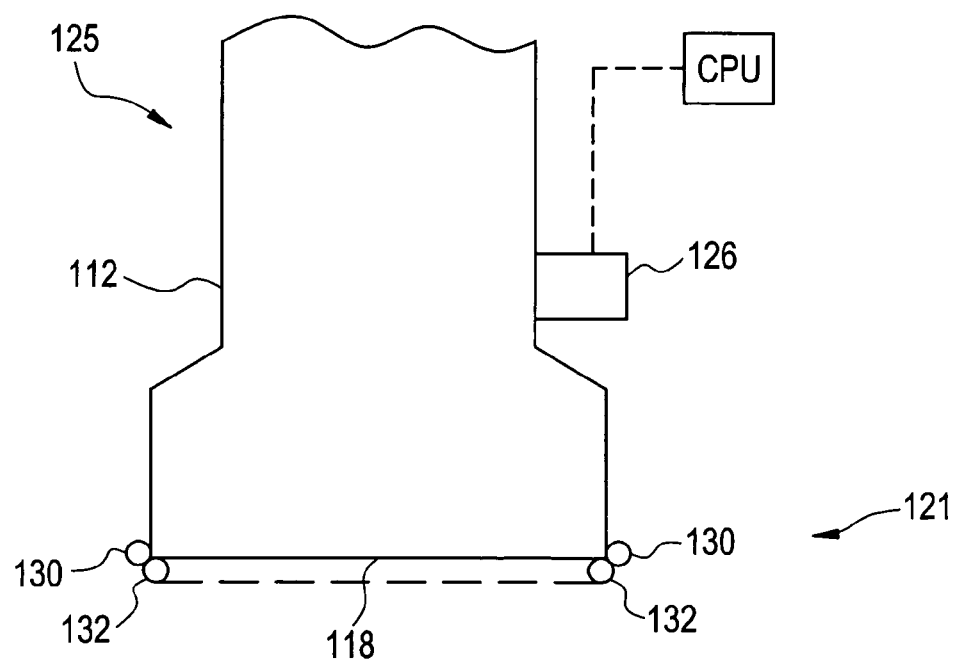
FIG. 4 illustrates a cross-sectional view of a center portion of an imaging device according to an alternative embodiment of the present invention.

Although the L-shaped bumper is preferred, another way for solving the problem of coverage created by a circular profile bumper is through the use of multiple bumpers. FIG. 4 illustrates an imaging device 125 according to alternative embodiment of the present invention. The imaging device includes a main body 112 with a distal end 121 defining an edge 118. A first bumper 130 encircles, and is adjacent to, the distal end 121 of the main body 112. A second bumper 132 is adjacent to, and extending laterally across the edge 118. Optionally, a third bumper (not shown) may be located between the first and second bumpers. The bumpers used in accordance with this alternative embodiment may have any geometric profile, including circular or oblong. Such an embodiment may solve the problem of coverage inherent in a system utilizing a single circular or oblong profile bumper.

Referring now to FIG. 8 (and FIGS. 2 and 4), an embodiment of the present invention may include a contact detection system 141 contained in a housing 126 attached to the main body 112 of the detector 110. The contact detection system 141 includes a pressure sensing device 143 and a switch. Suitable detection systems may include tape switches, micro switches, pressure transducers, and pressure wave switches. The pressure sensing device 143, which is in contact with the fluid contained in the bumper 120, detects pressure fluctuations in the bumper 120. The switch is then set to actuate in response to a certain measured pressure fluctuation. In the present embodiment, the detection system includes an on/off switch that is set to cut the power used to move the C-arm 106 when a certain pressure fluctuation occurs in the bumper. Other aspects of the invention may include detection systems that create a signal to notify an operator in the event of a pressure fluctuation. Still other aspects of the invention may include detection systems that create a signal, in response to a pressure fluctuation, which is sent to a processing unit 128 that may control the x-ray system 100. The processing unit 128 may be programmed to respond according to the signal. For example, in response to a signal indicating a pressure fluctuation, the processing unit may be programmed to move the C-arm in a desired direction or cut the power used to move the C-arm.

The detection system of the present invention may also include multiple pressure sensing devices with varying sensitivities. Such a system could produce multiple signals in response to pressure fluctuations in the bumper. Also, the detection system may include a pressure sensing device that measures the actual pressure in the bumper and creates a signal corresponding to the measured pressure. The signal(s) may be sent to a processing unit 128 that may be programmed to calculate certain characteristics of the system, such as the rate of pressure change in the bumper. The processing unit 128 may then be programmed to respond according to the signal(s) received and/or parameters calculated from the signals received.

Although FIG. 4 shows the detection system housing 126 on a lateral portion of the main body 112 (in close proximity to the bumper), the detection system can be located elsewhere. For example, another embodiment of the invention may include a detection system contained in a housing attached to the mobile support structure 102. The detection device is then connected to the bumper with a fluid tight hose, such that the fluid contained in the bumper is in contact with the fluid contained in the hose.

Figure 3:
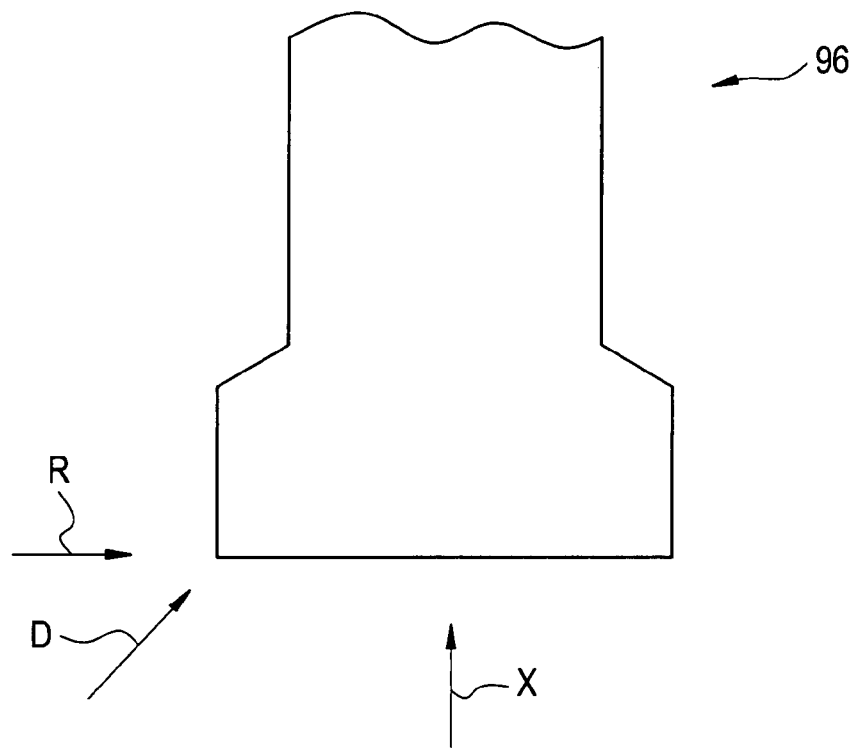
FIG. 3 illustrates a side view of a general imaging device.

It has been discovered that an L-shaped cushioned bumper has superior impact load distribution capabilities, superior pressure sensitivity, and more impact coverage than a circular or oblong shaped bumper. The L-shaped cushioned bumper has less volume and more surface area (i.e. a higher surface area to volume ratio) than a circular bumper for the same area of coverage, meaning that the L-shaped cushioned bumper experiences a greater pressure fluctuation in the event of an impact. Contact to the patient, therefore, may be detected earlier with the L-shaped cushioned bumper than a circular profile bumper. In addition, the L-shaped cushioned bumper provides coverage for contact in multiple directions (such as the radial R, axial X, and diagonal D directions shown in FIG. 3). Further, because the L-shaped bumper cushioned has a lower volume than currently used profiles, such as circular profiles, the L-shaped cushioned bumper allows the imaging device to come within close proximity to a patient, thereby allowing for high quality images.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A medical imaging system comprising:
    an imaging device having a lateral surface and a lower surface;
    a patient positioning area in close proximity to said imaging device,
    said imaging device being configured to move within said patient positioning area; and
    a protective bumper attached to said imaging device, said protective bumper conforming to a shape of a portion of said imaging device, wherein said protective bumper comprises (i) a first cushioned member positioned around at least a portion of said lateral surface of said imaging device; (ii) a second cushioned member positioned over at least a portion of said lower surface of said imaging device; and (iii) a third cushioned member positioned between said first cushioned member and said second cushioned member.

2. The medical imaging system of claim 1, wherein at least one of said first, second, and third cushioned members is an L-shaped cushioned bumper.

3. The medical imaging system of claim 2, wherein said protective bumper is fluid filled.

4. The medical imaging system of claim 3, further comprising a detection system in contact with said fluid, said detection system comprising a pressure sensing device.

5. The medical imaging system of claim 4 further comprising a housing mounted on said imaging device, said detection system being contained in said housing.

6. The medical imaging system of claim 4 wherein said detection system comprises a plurality of pressure sensing devices in contact with said fluid.

7. The medical imaging system of claim 4 wherein said detection system is electrically connected to a processing unit.

8. The medical imaging system of claim 1, wherein said imaging device comprises an x-ray source and an x-ray detector.

9. The medical imaging system of claim 1, wherein said medical imaging system is at least one of a CT, ultrasound, fluoroscopy, PET, and nuclear imaging system.

10. The medical imaging system of claim 1, wherein said imaging device is positioned on a C-arm and is configured to rotate around a patient positioned in said patient positioning area.

11. The medical imaging system of claim 1, wherein said imaging device includes a main body having a distal end having a lower surface, said protective bumper further comprising a first lip adjacent to said main body and a second lip extending laterally across said lower surface, wherein said first and second lips define a unitary structure.

12. A medical imaging device having a main body extending from a support structure, comprising:
 a first cushioned bumper positioned around at least a portion of a lateral surface of said main body;
 a second cushioned bumper positioned over at least a portion of a lower surface of said main body; and
 a third cushioned bumper positioned between said first cushioned bumper and said second cushioned bumper.

13. The medical imaging device of claim 12, wherein said first and second cushioned bumpers are fluid filled, further comprising: a housing, mounted on said imaging device; a detection system contained within said housing, said detection system comprising a pressure sensing device in contact with said fluid.

* * * * *